United States Patent
Greenbank et al.

(10) Patent No.: US 6,826,253 B2
(45) Date of Patent: Nov. 30, 2004

(54) X-RAY ANALYSIS APPARATUS

(75) Inventors: Michael Geoffrey Holmes Greenbank, Irlam (GB); Andrew Martin Watts, Congleton (GB); Peter John Hardman, Stockport (GB); Karl-Eugen Mauser, Bietigheim (DE)

(73) Assignee: Bruker AXS GmbH, Karlsruhe (DE)

( * ) Notice: Subject to any disclaimer, the term of this patent is extended or adjusted under 35 U.S.C. 154(b) by 196 days.

(21) Appl. No.: 10/214,121

(22) Filed: Aug. 8, 2002

(65) Prior Publication Data
US 2003/0048870 A1 Mar. 13, 2003

(30) Foreign Application Priority Data
Sep. 7, 2001 (DE) .......................................... 101 43 991

(51) Int. Cl.⁷ .......................................... G01N 23/223
(52) U.S. Cl. .......................... 378/44; 378/79; 378/208
(58) Field of Search .............................. 378/44–49, 79, 378/208

(56) References Cited

U.S. PATENT DOCUMENTS

| | | |
|---|---|---|
| 4,669,771 A | 6/1987 | Finneran |
| 4,770,593 A | 9/1988 | Anderson |
| 5,216,243 A * | 6/1993 | Varjonen et al. ............ 250/328 |
| 6,111,930 A | 8/2000 | Schipper |

FOREIGN PATENT DOCUMENTS

| | | |
|---|---|---|
| DE | 26 07 055 | 9/1977 |
| DE | 35 12 459 | 10/1986 |
| DE | 43 19 061 | 12/1993 |
| DE | 44 10 781 | 10/1994 |
| DE | 198 40 055 | 3/2000 |
| DE | 198 51 501 | 9/2000 |
| WO | WO 93/20612 | 10/1993 |
| WO | WO 87/06008 | 10/1997 |

OTHER PUBLICATIONS

"Spectrometry Solutions; S4 Explorer" Bruker AXS Analytical X–Ray Systems GmbH, Karlsruhe, 2001, 1 page only.

* cited by examiner

*Primary Examiner*—Craig E. Church
(74) *Attorney, Agent, or Firm*—Paul Vincent

(57) ABSTRACT

An X-ray analysis apparatus for investigating material samples, comprising a device for automatic exchange of the samples (1), which comprises a sample table (2) with depositing positions (3) disposed in m lines, wherein the lines extend parallel to an x direction and $m \geq 2$, and comprising a gripping device (4) for precise removal of any desired sample (1) from a depositing position (3) and for transfer into a transfer and/or measuring position (5) and back to a depositing position (3), wherein the gripping device (4) can be displaced linearly parallel to the x direction, is characterized in that the sample table (2) can be moved linearly parallel to a y direction, extending at an angle α to the x direction, and independently of the gripping device (4) for gripping samples (1) from different lines, wherein the sample table (2) is disposed parallel to the x-y plane. The inventive X-ray analysis device can have very simple topological construction and facilitates a considerably more compact structure requiring considerably less space while maintaining full relative motion of the parts. Access to the depositing, transfer and measuring positions is not limited compared to a conventional device.

14 Claims, 3 Drawing Sheets

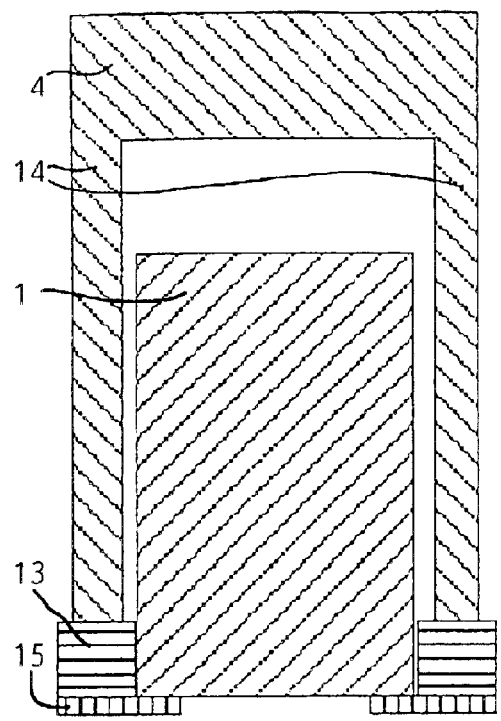
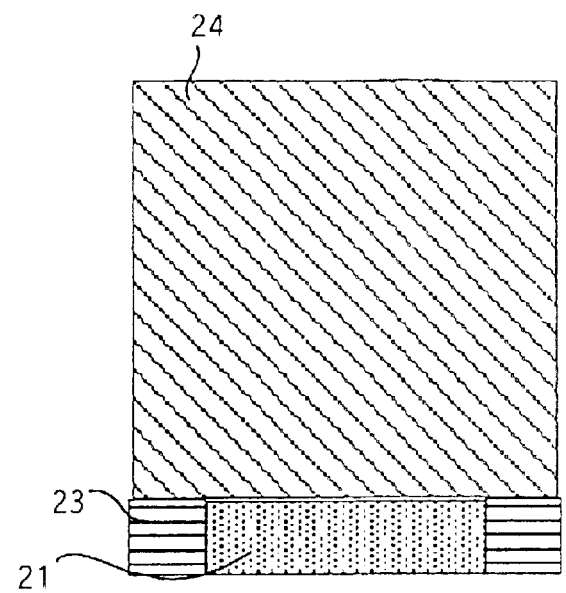
Fig. 3
Fig. 5
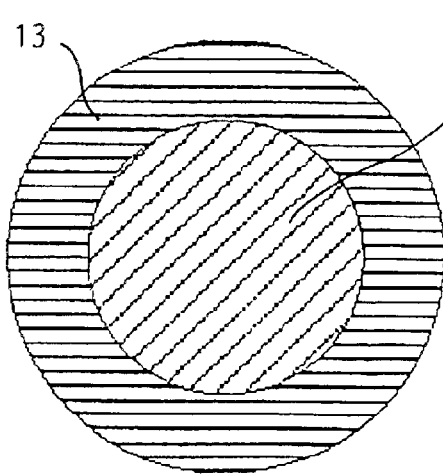
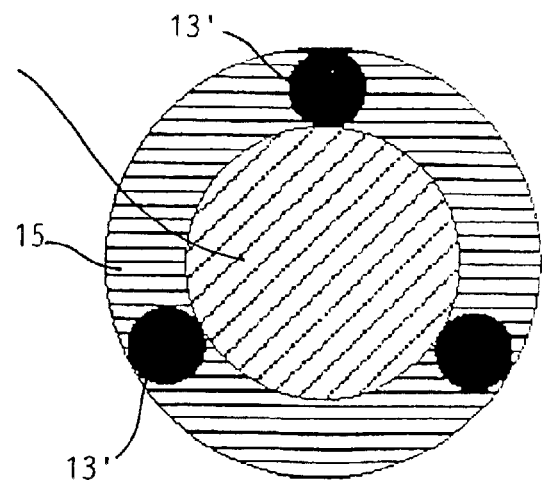
Fig. 4a
Fig. 4b

X-RAY ANALYSIS APPARATUS

This application claims Paris Convention priority of DE 101 43 991.1 filed Sep. 7, 2001 the complete disclosure of which is hereby incorporated by reference.

BACKGROUND OF THE INVENTION

The invention concerns an X-ray analysis apparatus for investigating material samples having a device for automatic exchange of the samples which contains a sample table with depositing positions disposed in m lines, wherein the lines extend parallel to an x direction and $m \geq 2$, and with a gripping device for precise removal of any desired sample from a depositing position and transferral into a transfer and/or measuring position and back to a depositing position, wherein the gripping device can be linearly displaced parallel to the x direction.

An X-ray analysis apparatus of this type is known e.g. from the company leaflet "SPECTROMETRY SOLUTIONS; S4 EXPLORER", Bruker AXS Analytical X-Ray Systems GmbH, 2001.

This document describes in detail the functional principles of an arrangement of this type. Such X-ray analysis apparatus are suited for rapid, routine, and non-destructive analyses of the most different of sample material in laboratories and research institutes. X-ray fluorescence, X-ray diffractometry, or other X-ray analysis methods can be used for examining the material samples. The material samples may be massive solid bodies, powder, or liquid samples disposed in appropriate sample containers.

Analysis devices of this type are provided for routine, rapid examination of a large number of samples. For this reason, an automatic exchange device must be provided for transporting, within the device, each of a plurality of samples to be examined. The known devices comprise a sample table for receiving the samples which is immovably fixed in the apparatus as e.g. described in the above-cited company leaflet. This sample table has openings defining an m×n matrix for inserting the different samples or sample containers. These are filled manually with the different samples according to a plan determined by the user before starting a measuring series which subsequently runs automatically without further manual influence on the part of the user.

Towards this end, the X-ray analysis apparatus comprises a gripping device for precise removal of any desired sample from one of the depositing positions, transfer into a transfer or measuring position and return back into the depositing position. To be able to address all positions on the rigid, rectangular sample table, the gripping device drive mechanism must be relatively complicated. The gripping robot must be movable in both the x and y directions. Gripping operations with the robot arm also require a substantial amount of space in the vertical z direction.

Taken together, the gripping device and the sample table, immovably mounted in the apparatus, occupy a very large, cuboid three-dimensional volume within the X-ray analysis apparatus. Since the device should also be used for routine examinations at locations where space is often quite limited, convenient use of an arrangement of this type with its associated operating elements in a typical working location is frequently problematic.

In view of the above, it is the underlying purpose of the invention to introduce an X-ray analysis apparatus with the above-mentioned features having simple topological construction which requires considerably less space due to a considerably more compact construction thereby maintaining full relative mobility of the parts, wherein accessibility to depositing, transfer and measuring positions is not less than that of the conventional device.

SUMMARY OF THE INVENTION

This object is achieved in accordance with the invention in a surprisingly simple and also effective fashion in that the sample table can be moved linearly, independently of the gripping device and parallel to a y direction extending at an angle $\alpha$ with respect to the x direction for gripping samples from different lines, with the sample table being disposed parallel to the x-y plane.

In this manner, construction of an X-ray analysis apparatus of this type is facilitated using means which are technically easy to realize. The available space can be used much more economically and the required space in the upper region of the apparatus can be considerably reduced without having to reduce the number of sample table depositing positions which can be addressed relative to conventional devices. This is possible since the gripping robot of the inventive apparatus must no longer be moved in both the x and y directions but only in the x direction. The sample table can be linearly displaced in the y direction relative to the robot such that the gripper can address any desired depositing position.

In the inventive X-ray analysis apparatus, the angle is preferably $\alpha \approx 90°$. This minimizes the space required for the gripping device and sample table and matches them to the geometry of conventional housings.

A geometric construction of the inventive X-ray analysis apparatus is also preferred with which the x-y plane extends horizontally. This permits optimum utilization of gravity during the gripping process. Moreover, liquid samples can be easily processed without the danger of spilling.

In a particularly preferred embodiment of the inventive X-ray analysis apparatus, the depositing positions are disposed on the sample table in the form of a matrix. Selection of the depositing positions by the user is simple and the sample table can be provided with a clear arrangement of samples for inserting the samples according to a system provided by the user. Moreover, addressing of a matrix of this type by the control software for the automatic gripping device is particularly straightforward.

To facilitate operation and to stock further sample tables with samples should there be a large number of samples to be examined, the sample tables are usually constructed such that they can be easily introduced into the X-ray analysis apparatus and be detachably mounted. Several sample tables can be provided for a given apparatus, wherein only one of them is mounted in the apparatus for the next measuring sequence. As an alternative or supplement, the inventive X-ray analysis apparatus can be designed such that the samples are introduced individually via an opening from the outside to a certain location of the sample table defined as the input position and are further transported from that location by the gripping device to depositing positions predetermined by the user.

One embodiment of the inventive X-ray analysis apparatus is particularly preferred with which the device for automatic exchange of the samples is housed in a common housing with the X-ray analysis apparatus. This permits particularly advantageous utilization of the above-mentioned advantages of the reduced space required for the gripping device due to the considerably more compact arrangement as facilitated by possible separation of x and y motion.

A particularly preferred further development of this embodiment is characterized in that the common housing tapers relative to the y direction towards the top in the direction of a vertical z axis which extends perpendicular to the x-y plane, wherein the gripping device is disposed in the upper tapering part of the housing. This can only be achieved with the inventive arrangement since the inventive gripping robot is only displaced in the x and not in the y direction. The space saved in the y direction in the upper part of the device can be utilized e.g. to install a monitor which would otherwise take up valuable space at another location in the operating chamber.

A further particularly preferred embodiment of the inventive X-ray analysis apparatus is characterized in that at least some of the samples are surrounded by a sample holder in the peripheral direction, wherein the respective sample or a container holding the sample projects past the sample holder in the direction of a vertical z direction, perpendicular to the x-y plane, the gripping device being disposed on that side of the sample to surround the parts of the sample or of the container holding the sample which project past the sample holder in an operating position in the z direction and grasp the sample holder.

The samples or sample containers of an X-ray analysis apparatus of this type are usually dimensioned such that they terminate at the upper edge of the sample holder in the z direction (see e.g. DE 198 51 501 C1). The sample-sided part of the gripping device thereby abuts the upper edge of the sample and of the sample holder during the gripping process. The above embodiment of the invention facilitates processing of samples extended in the z direction, e.g. liquid containers. This simplifies the loading and unloading of a sample holder having such samples extended in the z direction. Moreover, a gripping system of this kind can also easily grip conventional samples. This embodiment of the invention can therefore be used universally for the most different kinds of samples. While conventional systems have required special solutions for samples extended in the z direction, the above embodiment of the invention permits standardization of a very simple sample holder and use thereof at minimum cost.

In a particularly preferred further development of this embodiment, the sample holder comprises one (or several) holding section(s) disposed adjacent to the bottom-sided end of the sample or of the sample container to engage behind the sample or the sample container in a plane which is parallel to the x-y plane and act as mechanical stop in the z direction for the sample or sample container. This further facilitates loading the sample holder with the sample to obtain a defined, final position in the z direction.

The sample holder usually surrounds the sample annularly, preferably circularly, on its side facing the gripping device during operation. The sample or the sample container can then either be inserted or pressed into the sample holder ring.

In a further development of the invention, the sample holder comprises several parallel rods extending in the z direction which surround the sample in the peripheral direction on its side facing the gripping device during operation. This facilitates centering of the sample and extension of the rods in the z direction also provides a certain flexibility for deflection in the x-y plane during insertion of the sample to prevent damage to the sample due to excessive loading when pressed into the sample holder.

In a complementary fashion, the gripping device can also comprise at least three parallel rods which are preferably distributed uniformly about the periphery of the sample to be held and which extend in the z direction.

In embodiments of the invention, the gripping device can be operated mechanically. Although a gripping robot of this type is simple and inexpensive to manufacture, it is not very compact and requires significant amounts of space. In particular, relatively large amounts of sideward space are usually required in the horizontal x-y plane for a mechanical gripping process. The depositing positions of the samples in these embodiments must consequently have corresponding mutual separations to ensure safe gripping of the samples in the sample holder without contacting neighboring samples.

Alternatively or additionally, the gripping device can be operated pneumatically, preferably through suctioning the sample holders by underpressure. A pneumatically actuated mechanical gripper is also possible with which the pneumatic gripping, suctioning process must be carried out only at locations with particularly little space. In this case, the pneumatic device may serve both parts of the gripping system.

In a further development of this embodiment, the gripping device comprises rod-shaped gripping elements disposed on the side of the sample (as in an above-mentioned embodiment), wherein at least some of the parallel rods extending in the z direction can define suction nozzles for suctioning parts of the sample holder. In any case, an arrangement of this type requires considerably less space than a mechanical gripping arrangement since the parallel rods must not deflect in the x-y plane during the gripping process but can be rigidly lowered onto the sample holder in the z direction from above.

Embodiments of the invention are particularly preferred with which the gripping device is operated magnetically. The production of a magnetic means of this type is usually more expensive than a mechanical means but can be designed much more compactly.

In most of these embodiments, the gripping device is an electromagnet which can be externally controlled with electrical currents for activating and deactivating the gripping process.

In other further developments of this embodiment, the gripping device can have permanent magnetic sections on its side facing the sample holder during operation. A magnetic gripping device of this type is somewhat less demanding than an electromagnet, however a device for mechanical displacement of the permanent magnetic sections in the z direction must be provided for separating the grasped sample when depositing into the respective target position.

In a particularly preferred further development of the invention, the sample holder is formed at least partially of magnetizable, preferably ferromagnetic material on its side facing the gripping device during operation such that attraction and gripping thereof by means of a magnetic gripping device is particularly simple.

Further advantages can be extracted from the drawings and the description. The features mentioned above and below can be used in accordance with the invention either individually or collectively in any arbitrary combination. The embodiments shown and described are not to be understood as exhaustive enumeration but rather have exemplary character for describing the invention.

The invention is shown in the drawings and is explained in more detail by means of embodiments.

BRIEF DESCRIPTION OF THE DRAWING

FIG. 3 shows a schematic horizontal section through an inventive gripping device comprising a sample which is accommodated within an annular sample holder designed in accordance with the invention;

FIG. 4a shows a top view onto the sample with sample holder according to FIG. 3;

FIG. 4b shows a top view onto a sample with rod-shaped sample holder and annular holding section; and FIG. 5 shows a schematic vertical section through a gripping device with sample and sample ring according to prior art.

DESCRIPTION OF THE PREFERRED EMBODIMENT

Figure 1:
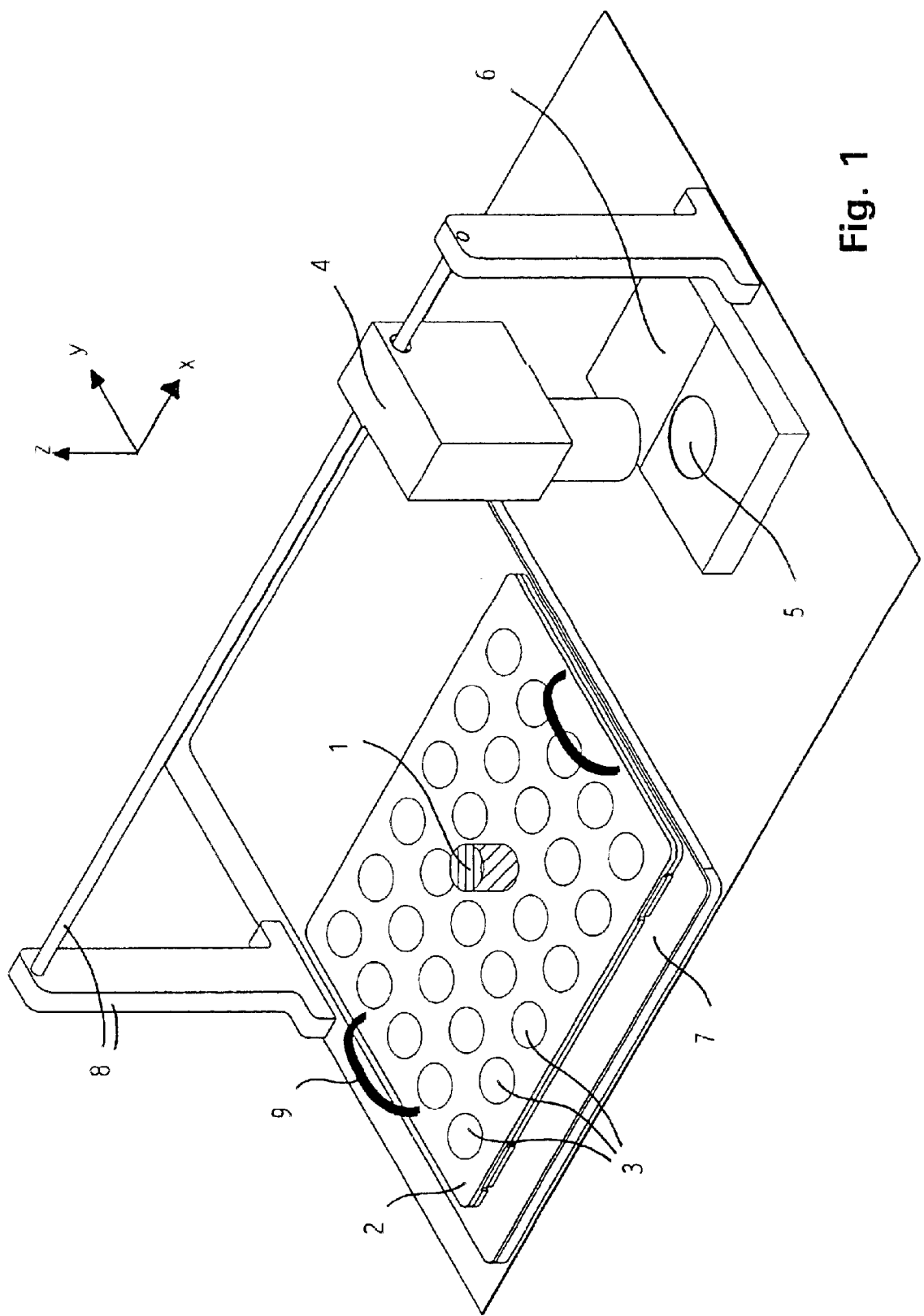
FIG. 1 schematically shows the gripping device of the linearly displaceable sample table and of the measuring position in an inventive X-ray analysis apparatus.

FIG. 1 schematically shows part of the "innards" of an inventive X-ray analysis apparatus. The one single sample 1 on a sample table 2 represents a plurality of samples to be examined. The sample table 2 contains depositing positions 3 disposed like a matrix in m lines, each of which can be provided with a sample.

A gripping device 4 is provided for precise removal of any desired sample 1 from a depositing position 3 in the sample table 2 and for transfer of the removed sample 1 to a measuring position 5. To protect the environment from X-ray radiation during operation, the measuring position 5 can be covered during the measurement by a radiation-shielding slider 6.

The gripping device 4 can be displaced on a frame 8 in the x direction along one of the m lines for access to any individual depositing position 3 in the sample table 2. The sample table 2 can be displaced linearly at a right angle thereto in the y direction on a rail plate 7. The sample table 2 is removably disposed on the rail plate 7 such that the samples can also be inserted manually into the depositing positions 3 from outside of the inventive X-ray analysis apparatus. The embodiment shown comprises two handles 9 for removing the sample table 2 from the apparatus.

Figure 2:
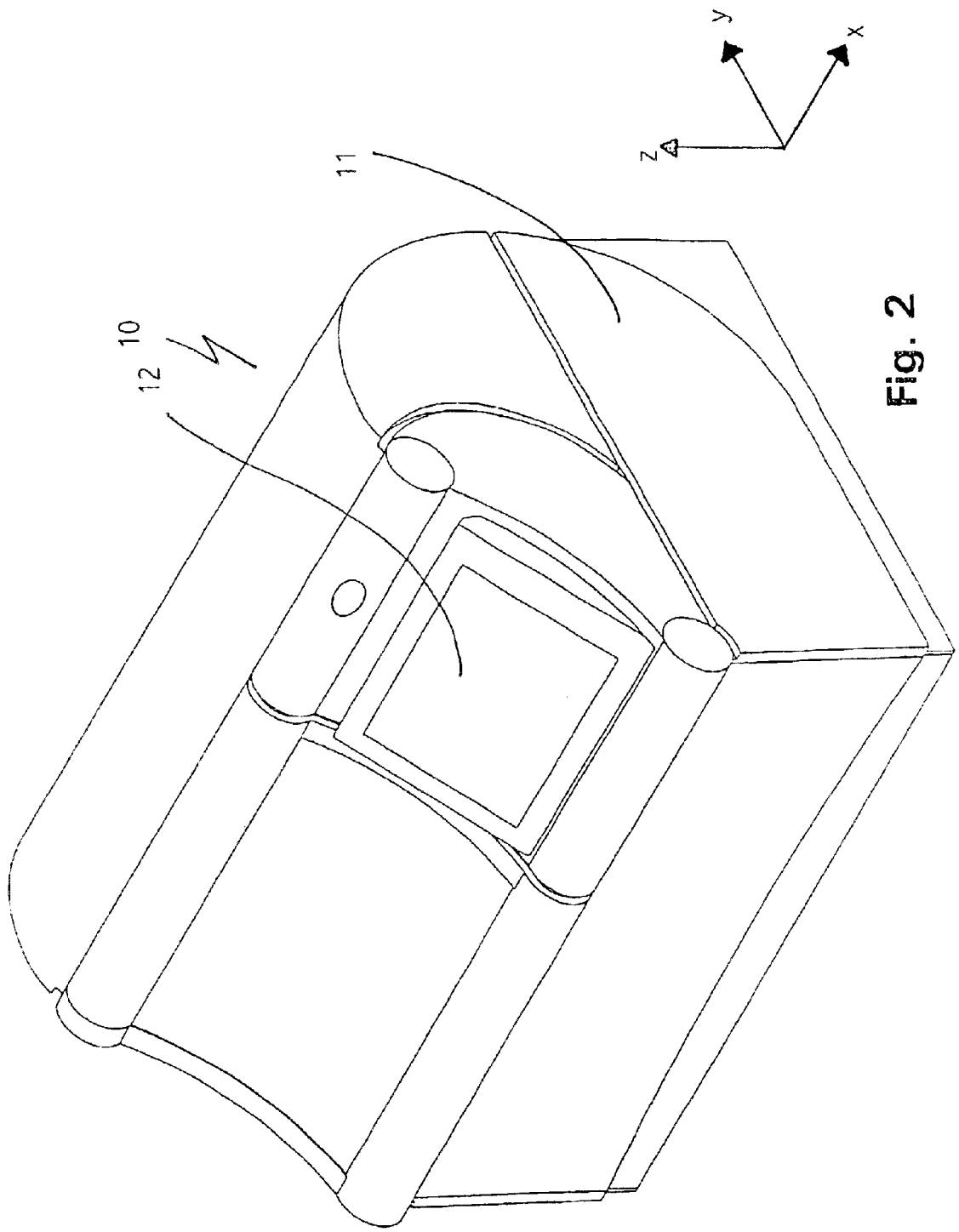
FIG. 2 schematically shows the housing for an embodiment of the inventive X-ray analysis apparatus with installed monitor.

FIG. 2 shows an inventive X-ray analysis device 10 which accommodates the parts shown in FIG. 1 inside its housing 11. Due to the separation between the x displacement of the gripping device 4 and the y displacement of the sample table 2 relative thereto, the housing 11 could be designed such that it tapers towards the top in the direction of the vertical z axis with respect to the y direction since, in accordance with the invention, the gripping device 4 must only move in the x and not in the y direction. In the embodiment shown, the saved space was used for installing a monitor 12 for the inventive X-ray analysis apparatus 10.

FIG. 3 shows, in a highly schematized fashion, a vertical section through a gripping device 4 which surrounds the sides of a sample 1 having a pronounced extension in the z direction with rods 14 and which is moved against a sample holder 13 annularly surrounding the sample 1. The bottom side of the sample holder 13 is connected to an annular holding section 15 which seats beneath the sample 1 to act as mechanical stop for the sample 1 in the z direction.

For gripping the sample holder 13 with the fitted sample 1, the rods 14 of the gripping device 4 can comprise magnets and the sample holder 13 magnetizable, preferably permanent magnetic material. The gripper 4 can thereby be an electromagnet or a permanent magnet.

Alternatively, the rods 14 of the gripping device 4 can define a suction nozzle for suctioning parts of the sample holder 13 and annularly surrounding the sample 1 (FIG. 4a).

Instead of rods 14, the gripping device 4 can have a tube-shaped end on the side of the sample, which must have an inside diameter larger than the outer diameter of the parts of the sample 1 projecting past the holding device 13 in the z direction. The tube-shaped end of the gripping device 4 can then be displaced in the z direction over the sample 1 to grip the sample holder 13.

As an alternative to the sample holder 13 shown in FIG. 4a, a sample holder 13' can be provided (FIG. 4b) having parallel rods extending in the z direction between which the sample 1 fits. As shown in the embodiment of FIG. 4b, a bottom side of the parallel rods of the sample holder 13' can be fixed to an annular holding section 15 which seats beneath the sample 1 on the bottom side (see FIG. 3) thereof.

In embodiments which are not shown in the drawing, the gripping device 4 can be operated mechanically instead of magnetically or pneumatically. The geometric construction of the sample-sided parts of the gripping device 4 would be similar to that of the embodiments shown.

Finally, by way of comparison, FIG. 5 schematically shows a gripping device 24 according to prior art which grips a sample ring 23 with fitted sample 21 (also according to prior art). In contrast to the embodiment shown in FIG. 3, the sample 21 ends flush with the sample ring 23 in the z direction (FIG. 5). For this reason, the sample-sided end of the gripping device 24 is not designed to permit lateral gripping of projecting parts of the sample.

We claim:

1. An X-ray analysis apparatus for investigating a plurality of sample materials with the assistence of a device for automatic exchange of the samples, the apparatus comprising:

a gripping device for removal of any desired sample from one of a plurality of deposit positions and for transfer of that sample to and from at least one of a transfer position and a measuring position, said gripping device having means for linear displacement thereof parallel to an x direction; and a sample table having said deposit positions disposed in m lines, said m lines extending parallel to said x direction and spaced apart from each other in a y direction extending at an angle of approximately 90 degrees relative to said x direction, wherein m≧z, said sample table having means for linear displacement thereof, independent of said gripping device, parallel to said y direction for gripping samples in different lines, said x and y directions lying in and defining an x-y plane, said sample table disposed parallel to said x-y plane.

2. The X-ray analysis apparatus of claim 1, wherein said depositing positions are disposed at said sample table in a matrix.

3. The X-ray analysis apparatus of claim 1, wherein said x-y plane extends horizontally.

4. The X-ray analysis apparatus of claim 1, further comprising a housing for common accommodation of said gripping device and said sample table.

5. The X-ray analysis apparatus of claim 4, wherein said housing tapers towards a top with respect to said y direction in a direction of a vertical z axis extending perpendicular to said x-y plane, said gripping device being disposed in an upper, tapering part of said housing.

6. The X-ray analysis apparatus of claim 1, further comprising sample holders surrounding at least some of said samples in a peripheral direction, said gripping device being structured and disposed to surround parts of said samples and to grip said sample holders.

7. The X-ray analysis apparatus of claim 6, wherein said sample holders comprises at least one holding section disposed adjacent to a bottom-sided end of said samples for engaging below said sample in a plane parallel to said x-y plane to act as a mechanical stop for said samples in said z direction.

8. The X-ray analysis apparatus of claim 6, wherein said sample holders surround said samples in one of an annular and circular fashion on sides thereof facing said gripping device during operation.

9. The X-ray analysis apparatus of claim 6, wherein said sample holders surround said samples on sides thereof facing said gripping device during operation and in a peripheral direction by means of several parallel rods extending in said z direction.

10. The X-ray analysis apparatus of claim 9, wherein at least one of said parallel rods which extend in said z direction defines a suction nozzle for suctioning parts of said sample holders for pneumatic operation of said gripping device.

11. The X-ray analysis apparatus of claim 9, wherein said gripping device comprises at least three parallel rods distributed about a periphery of said samples and extending in said z direction.

12. The X-ray analysis apparatus of claim 6, wherein said gripping device comprises an electromagnet.

13. The X-ray analysis apparatus of claim 12, wherein a side of said sample holders facing said gripping device during operation comprises magnetizable material.

14. The X-ray analysis apparatus of claim 13, wherein said magnetizable material is ferromagnetic.

* * * * *